United States Patent [19]

Amschler et al.

[11] Patent Number: 4,707,481
[45] Date of Patent: Nov. 17, 1987

[54] PYRIDAZINONES, THEIR PREPARATION AND USE, AND BRONCHOSPASMOLYTIC MEDICAMENTS CONTAINING PYRIDAZINONES

[75] Inventors: Hermann Amschler, Radolfzell; Wolf-Rüdiger Ulrich, Constance, both of Fed. Rep. of Germany

[73] Assignee: BYK Gulden Lomberg Chemische Fabrik GmbH, Constance, Fed. Rep. of Germany

[21] Appl. No.: 690,655

[22] PCT Filed: May 10, 1984

[86] PCT No.: PCT/EP84/00139

§ 371 Date: Jan. 4, 1985

§ 102(e) Date: Jan. 4, 1985

[87] PCT Pub. No.: WO84/04521

PCT Pub. Date: Nov. 22, 1984

[30] Foreign Application Priority Data

May 11, 1983 [CH] Switzerland ............ 2581/83

[51] Int. Cl.[4] .............. A61K 31/50; C07D 237/14
[52] U.S. Cl. ........................ 514/247; 544/239
[58] Field of Search .................. 514/247; 544/239

[56] References Cited

U.S. PATENT DOCUMENTS 4,397,854  8/1983  Sircar ........................ 424/250

FOREIGN PATENT DOCUMENTS 2614827 10/1977  Fed. Rep. of Germany ....... 544/239
2810267  9/1978  Fed. Rep. of Germany ....... 544/239

OTHER PUBLICATIONS

Derwent, #B03, 18917 K/08 for JP58008-015 (Chem. Ab. 98, 137630) 1983.
Derwent, #B03, 18918 K/08 for JP58008016 (Mitsubishi) 1983.
Derwent, #B02, 16839 C/10 for EP8391 (Thomae) 3/80.
Derwent, #B03C02 11413X/07 for DT2435244 (Lentia) 1974.
Derwent, #B03, 33034C/19 for EP10156 (Merck) 1980.
Derwent, B03 49295B/27, Hoechst for DT2757923, 1979.
Derwent, B03 67389A/38 for DT2810267 (Sankyo) 9/78.
Derwent, B03C02 30268X/17 DT2445681, Lentia, 4/76.
"Attorney's Dictionary of Patent Claims", vol. 1, pp. A-21, A-22.
Baddar et al., J. Chem. Soc., 3342–3348, 1965.
Steck et al., J. Heterocycl. Chem., vol. 11, 755–761, 1974.
Albright et al., J. Heterocycl. Chem., vol. 15, 881–892, 1978.
Schreiber et al., Bull. Soc. Chim., France, 2, 625–629, 1973.
Pitarch et al., Eur. J. Med. Chem.-Chimica Therapeutica, vol. 9, No. 6, 644–650, 1974.
Curran et al., J. Med. Chem., vol. 17, No. 3, 273–281, 1974.

Primary Examiner—Mark L. Berch
Attorney, Agent, or Firm—Berman, Aisenberg & Platt

[57] ABSTRACT

6-Aryl-3[2H]pyridazinones of the formula I

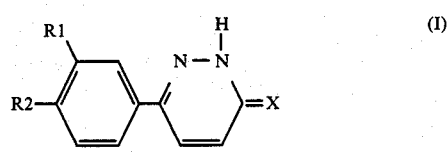

wherein one of the substituents R1 or R2 denotes methoxy and the other denotes (C2–C5)alkoxy or (C3–C5)alkenyloxy and X denotes oxygen or sulfur, and their pharmacologically acceptable salts with bases, are suitable for use as a bronchospasmolytic or cardiotonic agent. Processes for the preparation of the compounds and appropriate medicaments are described.

13 Claims, No Drawings

PYRIDAZINONES, THEIR PREPARATION AND USE, AND BRONCHOSPASMOLYTIC MEDICAMENTS CONTAINING PYRIDAZINONES

FIELD OF THE INVENTION

The invention relates to pyridazinones, their preparation and use, and medicaments containing pyridazinones.

PRIOR ART

6-Aryl-3[2H]pyridazinones as starting materials or intermediates for the synthesis of pharmaceuticals and plant protection agents and processes for their preparation are described, for example, by Baddar et al. [J.Chem. Soc. 1965, 3342], Steck [J.Heterocycl.Chem. 11(1974)755], Albright et al. [J.Heterocycl.Chem. 15(1978)881], Schreiber et al. [Bull.Soc.Chim.France 2(1973)625], Pitarch et al. [Eur.J.Med.Chem.-Chimica Therapeutica 9(1974)644] and Curran et al. [J.Med.-Chem. 17(1974)273], or are known, inter alia, from the following descriptions: German Offenlegungsschrift 2,435,244, German Offenlegungsschrift 2,445,681 and German Offenlegungsschrift 2,757,923.

6-Aryl-3[2H]pyridazinones with a certain action are known, for example, from the following descriptions: German Offenlegungsschrift 2,427,943, German Offenlegungsschrift 2,810,267, German Offenlegungsschrift 2,845,220, European Offenlegungsschrift 8,391, European Offenlegungsschrift 10,156, Japanese Preliminary Published Application 58,008,015 and U.S.Patent Specification 4,397,854.

6-(3,4-Dimethoxyphenyl)-3[2H]pyridazinone is described by Pitarch et al. and in German Offenlegungsschrift 2,810,267.

SUMMARY OF THE INVENTION

Certain 6-aryl-3[2H]pyridazinones of the general formula I now have an advantageous pharmacological action.

The invention relates to 6-aryl-3[2H]pyridazinones of the general formula I

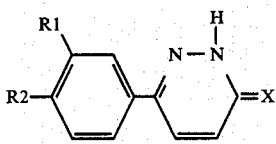

wherein one of the substituents R1 or R2 denotes a methoxy group and the other denotes an alkoxy group with 2 to 5 carbon atoms or an alkenyloxy group with 3 to 5 carbon atoms and X denotes an oxygen atom or a sulfur atom, and their parmacologically acceptable salts with bases.

Alkoxy and alkenyloxy are straight-chain or branched. The double bond of alkenyloxy does not start from the carbon atom bonded to the oxygen atom. Examples of alkoxy and alkenyloxy which may be mentioned are n-butoxy, n-propoxy, ethoxy, amyloxy, 2,2-dimethylpropyloxy, isopentyloxy, isobutoxy, sec.-butoxy, isopropoxy, buten-2-yloxy, allyloxy and methallyloxy; preferred alkoxy radicals contain 3 or 4 carbon atoms.

Possible salts are salts with inorganic and organic bases. Cations which are used for the salt formation are, in particular, the cations of the alkali metals or alkaline earth metals, but the corresponding cations of organic nitrogen bases, such as amines or aminoalkanols, aminosugars and the like, are also used. Examples which may be mentioned are the salts of sodium, magnesium, calcium, dimethylamine, diethylamine, ethanolamine, diethanolamine, triethanolamine, glucamine, N-methylglucamine, glucosamine and N-methylglucosamine.

6-Aryl-3[2H]pyridazinones of the general formula Ia

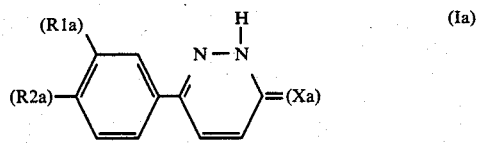

wherein

R1a denotes a methoxy group,

R2a denotes an alkoxy group with 2 to 4 carbon atoms or an alkenyloxy group with 3 or 4 carbon atoms and Xa denotes an oxygen atom, and their pharmacologically acceptable salts with bases, form an embodiment of the invention.

6-Aryl-3[2H]pyridazinones of the general formula Ib

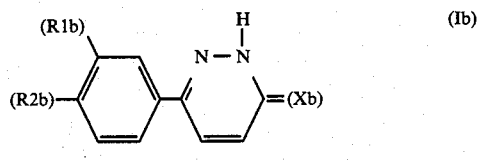

wherein

R1b denotes an alkoxy group with 2 to 4 carbon atoms or an alkenyloxy group with 3 or 4 carbon atoms, R2b denotes a methoxy group and Xb denotes an oxygen atom, and their pharmacologically acceptable salts with bases, form another embodiment of the invention.

Preferred representatives of embodiment Ia are those in which R2a represents an n-propoxy, isopropoxy or isobutoxy group. Particularly preferred representatives are the compounds 6-(3-methoxy-4-n-propoxyphenyl)-3(2H)pyridazinone and 6-(4-isobutoxy-3-methoxyphenyl)-3(2H)pyridazinone.

Preferred representatives of the embodiment Ib are those in which R1b represents an n-propoxy, isopropoxy, allyl or isobutoxy group. Particularly preferred representatives are the compounds 6-(3-isobutoxy-4-methoxyphenyl)-3[2H]pyridazinone and 6-(4-methoxy-3-n-propoxyphenyl)-3[2H]pyridazinone.

The invention also relates to the use of the compounds according to claim 1 for the treatment or prophylaxis of diseases which are based on disorders of the bronchi and/or cardiac insufficiency, or for strengthening the heart, and to the appropriate medicaments.

The compounds 6-(3-methoxy-4-n-propoxyphenyl)-3[2H]pyridazinone, 6-(4-isobutoxy-3-methoxyphenyl)-3[2H]-pyridazinone and 6-(4-methoxy-3-isopropoxyphenyl)-3[2H]pyridazinone are preferred for use for the treatment or prophylaxis of diseases which are based on disorders of the bronchi, and the two first-mentioned compounds are particularly preferred.

The compounds 6-(3-isobutoxy-4-methoxyphenyl)-3[2]pyridazinone, 6-(4-methoxy-3-n-propoxyphenyl)-3[2H]pyridazinone and 6-(3-allyloxy-4-methoxyphenyl)-3[2H]-pyridazinone are preferred for use for the treatment or prophylaxis of diseases which are based on cardiac insufficiency, or for strengthening the heart, and the first-mentioned compound is particularly preferred.

The preferred medicaments are those which contain compounds whose use is preferred.

The invention furthermore relates to a process for the preparation of the 6-aryl-3[2H]pyridazinones of the general formula I and their pharmacologically acceptable salts with bases, which is characterized in that (a) a 6-aryl-tetrahydropyridazinone of the general formula II

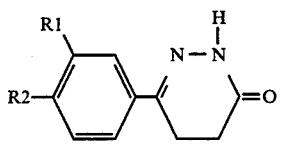

wherein R1 and R2 have the abovementioned meaning, is oxidized and, if desired, the resulting pyridazinone I (X=0) is then converted into the pyridazinethione I (X=S) and/or into the salt, or (b) a morpholinobutyric acid of the general formula III

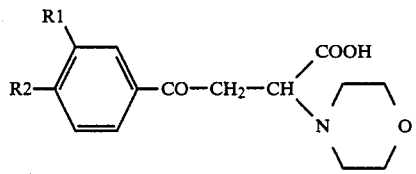

wherein R1 and R2 have the abovementioned meaning, is reacted with hydrazine and, if desired, the resulting pyridazinone I (X=0) is then converted into the pyridazinethione I (X=S) and/or into the salt, or (c) an acrylic acid of the general formula IV

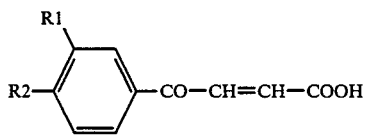

wherein R1 and R2 have the abovementioned meaning, is reacted with hydrazine and, if desired, the resulting pyridazinone I (X=0) is then converted into the pyridazinethione I (X=S) and/or into the salt.

The oxidation (dehydrogenation) according to process variant a) is carried out by methods which are known to the expert. For example, the dehydrogenation can be carried out in the presence of noble metals of sub-group 8, for example palladium or platinum [German Offenlegungsschrift 2,757,923]; with chromium trioxide [Overend et al. J.Chem.Soc. 1947, 239] or with nitrobenzenesulfonic acids or nitronaphthalenesulfonic acids, preferably with sodium or ammonium salts thereof [British Patent Specification 1,168,291].

The reaction according to process variant (b) is carried out by a method analogous to that of Schreiber et al. [Bull.Soc.chim.France 2(1973)625]. For example, the morpholinobutyric acid III is reacted with hydrazine hydrate under reflux in a lower alkanol, for example n-butanol. Alternatively, the morpholinium salt, of the compound III, obtained by reaction of the corresponding acetophenone with glyoxylic acid and morpholine can be reacted with hydrazine hydrate in acid solution.

The reaction according to process variant (c) is carried out by methods which are known to the expert. For example, the compounds IV are reacted, in a manner analogous to that in German Offenlegungsschrift 2,445,681, with methanol or aqueous methanol at room temperature or slightly elevated temperature in the presence of basic compounds, such as alkali metal carbonates, hydroxides or lower alkanolates or tert.-amines, the acid is liberated from the salt formed and this acid is heated with 1 to 1.5 moles of hydrazine hydrate, at least a neutral medium, but preferably an acid medium, being maintained.

The resulting arylpyridazinones I (X=oxygen) are converted into the arylpyridazinethiones I (X=sulfur) by methods which are known to the expert. For example, the arylpyridazinones I are reacted, in a manner analogous to that of Albright et al. [J.Heterocycl.Chem. 15(978)881], with phosphorus oxyhalides at 80°-120° C. in the presence of a solvent, such as toluene, xylene or chlorinated hydrocarbons, but preferably without a solvent, to give the corresponding 6-aryl-3-halogenopyridazines, reaction of which (Jahine et al. [Ind.J.Chem. 16B (1978)1000-1003]) with thiourea, for example by heating in a lower alkanol, such as n-butanol or methyl- or ethyl-cellosolve at 100° to 140° C. for 5-10 hours, leads to the arylpyridazinethiones I.

The 6-aryl-3[2H]pyridazinones I are converted into the salts by methods which are known to the expert. That inorganic or organic base, the salt of which is desired, is used as the alkaline reactant. The salts are obtained, for example, by reacting the pyridazinones I with the stoichiometric equivalent of the corresponding base, for example sodium hydroxide or sodium methanolate, or by converting readily soluble salts into sparingly soluble salts by double decomposition.

For the preparation of the new compounds Ia and Ib, corresponding starting compounds IIa, IIb, IIIa, IIIb, IVa or IVb

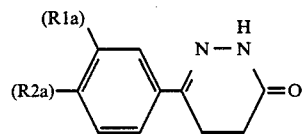

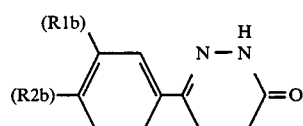

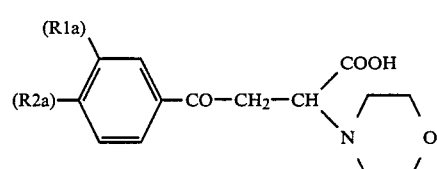

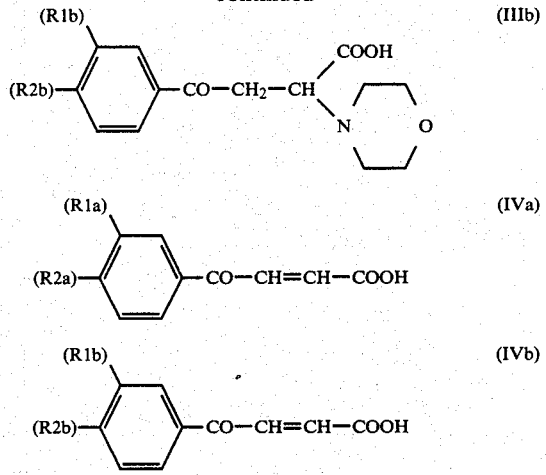

wherein R1a, R1b, R2a and R2b have the abovementioned meaning, are used.

The compounds II, III and IV are known, or they can be prepared by known processes.

The following examples serve to illustrate the invention in more detail. m.p. denotes melting point and the temperatures are given in °C.

Example 1:
6-(4-n-Butoxy-3-methoxyphenyl)-3[2H]pyridazinone 11.0 g of 6-(4-hydroxy-3-methoxyphenyl)-4,5-dihydro-3[2H]pyridazinone are heated under reflux together with 8.2 g of 1-bromobutane and 8.3 g of potassium carbonate in 150 ml of anhydrous acetone for 20 hours. Thereafter, the starting compound can no longer be detected by thin-layer chromatography. The suspension is filtered hot, the filter cake is washed out with hot acetone and the filtrates are combined and evaporated in vacuo. The semi-solid residue [6-(4-n-butoxy-3-methoxyphenyl)4,5-dihydro-3[2H]pyridazinone]is taken up in 50 ml of ethanol, 10.0 g of sodium hydroxide in 200 ml of water and 14.6 g of sodium meta-nitrobenzenesulfonate are added and the mixture is heated under reflux for 2 hours. After cooling, it is acidified to pH 1-2 with concentrated hydrochloric acid, the crystalline solid is filtered off with suction and the solution is extracted several times with chloroform. The residue from the chloroform extract is combined with the crystals and the product is recrystallized from ethanol/ethyl acetate. 8.7 g (63.7% of theory) of the title compound of m.p. 193° are obtained.

The following are obtained analogously: 6-(4-allyloxy-3-methoxyphenyl)-3[2H]pyridazinone, m.p. 165°, by reaction of 6-(4-hydroxy-3-methoxyphenyl)-4,5-dihydro-3[2H]pyridazinone with allyl bromide, and oxidation of the resulting 4,5-dihydro-3[2]pyridazinone.

Example 2:
6-(4-Ethoxy-3-methoxyphenyl)-3[2H]pyridazinone (a) 4.5 g of 4-(4-ethoxy-3-methoxyphenyl)-2-morpholino-4-oxobutyric acid are boiled under reflux in 30 ml of 1-butanol with 6.7 g of 100% pure hydrazine hydrate for 8 hours. The reaction mixture is then evaporated in vacuo; the residue is boiled up in 100 ml of 2N hydrochloric acid, filtered off with suction and washed with water until free from acid. After drying, 2.1 g (65.6% of theory) of the title compound of m.p. 182°-184° are obtained; after recrystallization from ethanol/ethyl acetate, the product has a melting point of 186°.

The following are obtained analogously: 6-(4-allyloxy-3-methoxyphenyl)-3[2H]pyridazinone, m.p. 165°; 6-(3-methoxy-4-n-propoxyphenyl)-3[2H]pyridazinone, m.p. 172°; 6-(4-n-butoxy-3-methoxyphenyl-3[2H]pyridazinone, m.p. 193°; 6-(4-ethoxy-3-methoxyphenyl)-3[2H]pyridazinone, m.p. 192°; by reaction of the corresponding 4-aryl-2-morpholino-2-oxobutyric acids with hydrazine hydrate.

(b) The 4-aryl-2-morpholino-4-oxobutyric acids used are prepared as follows:

8.7 g of glyoxylic acid monohydrate are boiled up in 50 ml of ethanol until solution is complete, 16.5 g of morpholine and 18.5 g of 4-ethoxy-3-methoxyacetophenone are then added and the mixture is stirred at 50° for 16 hours. The reaction mixture is evaporated in vacuo and the residue is digested with acetone, cooled, filtered off with suction and dried in vacuo. 9.9 g of morpholinium 4-(4-ethoxy-3-methoxyphenyl)-2-morpholino-4-oxobutyrate of m.p. 131° are obtained. To liberate the acid, the morpholinium salt is dissolved in 50 ml of water and the solution is acidified to pH 4.5 with acetic acid; the acid obtained as an oil is extracted with chloroform and the chloroform extract is dried over sodium sulfate and evaporated. The residue is digested with ethyl acetate, filtered off with suction and dried in vacuo. 4.9 g of the free acid of m.p. 157° are obtained.

In an analogous manner, morpholinium 4-(3-methoxy-4-n-propoxyphenyl)-2-morpholino-4-oxobutyrate, m.p. 110°; morpholinium 4-(4-n-butoxy-3-methoxyphenyl)-2-morpholino-4-oxobutyrate, m.p. 120°; 4-(4-allyloxy-3-methoxyphenyl)-2-morpholino-4-oxobutyric acid, m.p. 166°; morpholinium 4-(4-ethoxy-3-methoxyphenyl)-2-morpholino-4-oxobutyrate, m.p. 131°; 4-(4-ethoxy-3-methoxyphenyl)-2-morpholino-4-oxobutyric acid, m.p. 157° are prepared from the corresponding acetophenones.

Example 3:
6-(3-methoxy-4-n-propoxyphenyl)-3[2H]pyridazinone (a) 10.6 g of 3-(3-methoxy-4-n-propoxybenzoyl)acrylic acid and 6.1 g of potassium carbonate are dissolved in 100 ml of methanol and the solution is stirred overnight at room temperature. It is acidified with 7.4 ml of concentrated hydrochloric acid, 2.2 g of 100% pure hydrazine hydrate are added to the mixture and the mixture is boiled under reflux for 3 hours. It is then acidified to pH 1 with 1 ml of hydrochloric acid and 75 ml of methanol are distilled off in the course of 2 hours. The mixture is allowed to cool and the crystal mass is filtered off with suction, suspended several times in 50 ml of water each time, filtered off with suction and, finally, dried in vacuo. 6.6 g (63.7% of theory) of the title compound of m.p. 169°-171° are obtained. After recrystallization from ethanol/ethyl acetate, the m.p. rises to 172°.

In an analogous manner, 6-(4-n-butoxy-3-methoxyphenyl)-3[2H]pyridazinone, m.p. 193°; 6-(4-ethoxy-3-methoxyphenyl)- 3[2H]pyridazinone, m.p. 186°; 6-(4-sec.-butoxy-3-methoxyphenyl)-3[2H]pyridazinone, m.p. 168°, 6-[4-(3-methylbutoxy)-3-methoxyphenyl]-3[2H]pyridazinone, m.p. 170°, are obtained from the correspondingly substituted 3-benzoylacrylic acids.

(b) The 3-benzoylacrylic acids are prepared as follows:

10.4 g of (3-methoxy-4-n-propoxy)acetophenone are mixed with 9.2 g of glyoxylic acid monohydrate and the mixture is heated at 110° in an oil bath for 1 hour. The mixture is then boiled up with 200 ml of water, cooled and extracted with chloroform. For better phase separation, the aqueous phase is saturated with sodium chloride. After the chloroform extract has been dried over sodium sulfate and evaporated in vacuo, the orange-red residue is crystallized from acetone. 10.4 g (78.7% of theory) of 3-(3-methoxy-4-n-propoxybenzoyl)acrylic acid of m.p. 158° are obtained.

In an analogous manner, 3-(4-n-butoxy-3-methoxybenzoyl)acrylic acid, m.p. 136°, 92.5% of theory; 3-(4-ethoxy-3-methoxybenzoyl)acrylic acid, m.p. 154°, 95.3% of theory; 3-(4-methoxy-3-n-propoxybenzoyl)acrylic acid, 3-(3-ethoxy-4-methoxybenzoyl)-acrylic acid, 3-(3-allyloxy-4-methoxybenzoyl)acrylic acid, 3-[3-(3-methylbutoxy)-4-methoxybenzoyl]acrylic acid, 3-(4-sec.-butoxy-3-methoxybenzoyl)acrylic acid, m.p. 128°; 96% of theory and 3-[4-(3-methylbutoxy)-3-methoxybenzoyl]acrylic acid, m.p. 110°; 93.1% of theory, are obtained from the correspondingly substituted acetophenones.

(c) The substituted acetophenones are prepared as follows:

50 g of 4-hydroxy-3-methoxyacetophenone are dissolved in 100 ml of dimethylformamide, 94 g of an 80% strength sodium hydride/mineral oil suspension are added in portions and 40.7 g of n-propyl bromide, dissolved in 200 ml of dimethylformamide, are added to the solution when the evolution of hydrogen has ended. The solution is stirred at 100°for 2 hours and freed from the solvent in vacuo; the oily residue is partitioned between 2N sodium hydroxide solution and methylene chloride and the aqueous phase is extracted twice more with methylene chloride. After the combined organic extracts have been dried over potassium carbonate, they are evaporated in vacuo and the residue is crystallized from cyclohexane. 50.6 g (80.8% of theory) of 3-methoxy-4-n-propoxyacetophenone of m.p. 42° are obtained.

The following compounds are obtained in an analogous manner: 4-n-butoxy-3-methoxyacetophenone, m.p. 45°, 82% of theory; 4-ethoxy-3-methoxyacetophenone, m.p. 76°, 90.8% of theory; 4-allyloxy-3-methoxyacetophenone, boiling point 125°/0.133 mbar, 92.3% of theory; 4-isopropyloxy-3-methoxyacetophenone, m.p. 111°, 79.7% of theory; 4-sec.-butyloxy-3-methoxyacetophenone, oil, 95.5% of theory; 4-(3-methylbutoxy)-3-methoxyacetophenone, oil, 95.8% of theory; 4-methoxy-3-n-propoxyacetophenone, m.p. 71°, 68.7% of theory; 3-ethoxy-4-methoxyacetophenone, m.p. 67°, 74.3% of theory; 3-allyloxy-4-methoxyacetophenone, m.p. 49°, 77% of theory; 3-isopropyloxy-4methoxyacetophenone, m.p. 36°, 75.7% of theory; 3-(3-methylbutoxy)-4-methoxyacetophenone, oil, 65% of theory; 3-isobutoxy-4-methoxyacetophenone, m.p. 69°, 91.8% of theory, 4-isobutoxy-3-methoxyacetophenone, m.p. 38°, 91.8% of theory.

Example 4:
6-(3-Methoxy-4-n-propoxyphenyl)-3[2H]pyridazinethione.

(a) T13.9 g of 3-chloro-6-(3-methoxy-4-n-propoxyphenyl)pyridazine are boiled under reflux with 5.5 g of thiourea in 50 ml of ethylene glycol monomethyl ether for 8 hours. After cooling, the mixture is diluted with 250 ml of water and extracted three times with chloroform. The chloroform extracts are dried over sodium sulfate and evaporated. The residue is crystallized from ethanol/ethyl acetate. 4.8 g (34.6% of theory) of the title compound of m.p. 174°-17620 are obtained.

The following compounds are obtained in an analogous manner: 6-(3-ethoxy-4-methoxyphenyl)-3[2H]pyridazinethione, m.p. 183°, 88.9% of theory; 6-(3-isopropoxy- 4-methoxyphenyl)-3[2H]pyridazinethione, m.p. 168°, 93.4% of theory; 6-(3-isobutoxy-4-methoxyphenyl)3[2H]pyridazinethione, m.p. 170°, 66.7% of theory; 6-(4-isobutoxy-3-methoxyphenyl)-3[2H]pyridazinethione, m.p. 145°, 100% of theory.

(b) 29.9 g of 6-(3-methoxy-4-n-propoxyphenyl)-3[2H]pyridazinone are introduced in portions into 65 ml of phosphorus oxide-trichloride, with stirring, and the mixture is then stirred at 100° for 1 hour. The reaction mixture is concentrated to half in vacuo and poured onto ice, with thorough stirring. The crystals which deposit are filtered off with suction, washed with water and dried in vacuo. 31.6 g of 3-chloro-6-(3-methoxy-4-n-propoxyphenyl)pyridazine are obtained.

The following compounds are obtained in an analogous manner: 3-chloro-6-(3-ethoxy-4-methoxyphenyl)-pyridazine, m.p. 141°, 63.9% of theory; 3-chloro-6-(3-isopropoxy-4-methoxyphenyl)pyridazine, m.p. 144°, 94.9% of theory; 3-chloro-6-(3-isobutoxy-4-methoxyphenyl)pyridazine, m.p. 137°, 96.1% of theory; 3-chloro-6-(4-isobutoxy-3-methoxyphenyl)pyridazine, m.p. 116°, 95.8% of theory.

Example 5: The sodium salt of 6-(3-methoxy-4-n-propoxyphenyl)-3[2H]pyridazinone 26 g of 6-(3-methoxy-4-n-propoxyphenyl)-3[2H]pyridazinone are stirred in 150 ml of methanol with 60 g of sodium methylate (97% pure) at 50° for 30 minutes and the mixture is then evaporated to dryness in vacuo. The colorless residue is extracted by boiling with ethanol. After drying, 24.8 g (87.9% of theory) are obtained as a colorless solid which does not melt up to 280°.

Example 6:
6-(3-Isopropoxy-4-methoxyphenyl)-3[2H]pyridazinone 9.1 g of 3-isopropoxy-4-methoxyacetophenone are mixed with 4.0 g of glyoxylic acid monohydrate, and the mixture is heated at 110° for 1.5 hours. After cooling to 50° C., the melt is diluted with 30 ml of water, and the mixture is made alkaline with 10 ml of concentrated aqueous ammonia solution. After addition of 2.2 g of hydrazine hydrate, the solution is boiled under reflux for 2 hours, the title compound separating out as crystals. After cooling the suspension, the latter is filtered off with suction, and the filter cake is washed with water to neutrality and dried in vacuo. After recrystallization from ethyl acetate, 8.5 g (75.2% of theory) of the title compound, of m.p. 160°, are obtained.

The following are obtained analogously: 6-(4-isobutoxy-3-methoxyphenyl)-3[2H ]pyridazinone, m.p. 184°, 42.2% of theory, 6-(3-isobutoxy-4-methoxyphenyl)-3[2H]pyridazinone, m.p. 186°, 58.4% of theory, 6-(3-ethoxy-4-methoxyphenyl )-3[2H]pyridazinone, m.p. 171°, 73.1% of theory and 6-(3-methoxy-4-n-propoxyphenyl)-3[2H ]pyridazinone, m.p. 173°, 66.3% of theory.

Example 7:
6-[4-Methoxy-3-(3-methylbutoxy)phenyl]-3[2H]pyridazinone 18 g of 4-methoxy-3-(3-methylbutoxy)acetophenone and 7.7 g of glyoxylic acid monohydrate are mixed and the mixture is heated at 110° for 1.5 hours. After cooling, the melt is dissolved in 50 ml of methanol, 11.6 g of potassium carbonate are added, and the mixture is stirred overnight at 20°-25°. The mixture is then neutralized with 84 ml of 1N hydrochloric acid, 4.2 g of hydrazine hydrate are added, and the mixture is boiled under reflux for 3 hours. Finally, it is acidified to pH 1 with 20 ml of concentrated hydrochloric acid, again briefly boiled up, and the reaction mixture is largely freed from methanol in vacuo. The resulting reaction product, which is partly an oil and partly crystalline, is extracted with chloroform, and the combined extracts are dried over sodium sulfate and evaporated in vacuo. After recrystallization of the residue from isopropanol, 9.6 g (43.8% of theory) of the title compound, of m.p. 192°, are obtained.

The following are obtained analogously: 6-(4-methoxy-3-n-propoxyphenyl)-3[2H]pyridazinone, m.p. 196°, 17.5% of theory, 6-(3-allyloxy-4-methoxyphenyl)-3[2H]pyridazinone, m.p. 175°, 16.3% of theory, 6-(3-ethoxy-4-methoxyphenyl)-3[2H]pyridazinone, m.p. 171°, 15.1% of theory and 6-(4-isopropoxy-3-methoxyphenyl)-3[2H]pyridazinone, m.p. 200°, 26.4% of theory.

Commercial usefulness

The 6-aryl-3[2H]pyridazinones of the general formula I and those of embodiments Ia or Ib have valuable properties which render them commercially useful. Surprisingly, they are distinguished by a bronchospasmolytic and/or cardiotonic action which is in some cases considerably superior to that of theophylline or theophylline-ethylenediamine. They also have a more powerful bronchospasmolytic or positive inotropic action than 6-(4-methoxyphenyl)-3[2H]pyridazinone.

The bronchospasmolytic activity of the 6-aryl-3[2H]pyridazinones enables them to be used in human and veterinary medicine, where they are used for the treatment and prophylaxis of diseases based on disorders of the bronchi. For example, chronic obstructive respiratory diseases of various origins (bronchitis or bronchial asthma) can be treated in humans and animals.

The positive inotropic activity of the 6-aryl-3[2H]pyridazinones enables them to be used in human or veterinary medicine, where they are used for the treatment of diseases which are based on cardiac insufficiency or for strengthening the heart. For example, myocardial insufficiency, cardiac insufficiency, geriatric heart, myocardial infarction, cardiovascular insufficiency, angina pectoris with deficient cardiac output and coronary insufficiency are treated in humans and animals.

The invention thus furthermore relates to a method of treating mammals suffering from one of the abovementioned diseases. The method is characterized in that a therapeutically effective and pharmacologically acceptable amount of one or more of the compounds according to the invention is administered to the diseased mammal.

The invention also relates to medicaments containing one or more of the 6-aryl-3[2H]pyridazinones of the general formula I or of embodiments Ia or Ib.

The medicaments are prepared by processes which are known per se, the compounds being used as such or, if appropriate, in combination with suitable pharmaceutical excipients. If the new pharmaceutical formulations contain pharmaceutical excipients in addition to the active compounds, the content of active compound in these mixtures is 0.5 to 95, preferably 15 to 75, per cent by weight of the total mixture.

The active compounds or the medicaments are used in any suitable formulation, provided that the establishment and maintenance of sufficient levels of active compound are ensured. This can be achieved, for example, by oral or parenteral administration in suitable doses. The pharmaceutical formulation of the active compound is usually in the form of unit doses appropriate for the desired administration. A unit dose can be, for example, a tablet, a coated tablet, a capsule, a suppository or a measured volume of a powder, of a granular material, of a solution, of an emulsion or of a suspension.

"Unit dose" in the context of the present invention is understood as a physically discrete unit which contains an individual amount of the active constituent in combination with a pharmaceutical excipient, the content of active compound in the unit dose corresponding to a fraction or multiple of a therapeutic individual dose. An individual dose preferably contains the amount of active compound which is given in one administration and which usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention can contain about 5 to 250 mg, advantageously 10 to 200 mg and in particular 20 to 100 mg, of active compound. Parenteral formulations can contain about 1 to 50 mg, advantageously 3 to 30 mg and in particular 5 to 25 mg, of active compound.

In human medicine, the active compound or compounds, when these are given orally, are in general administered in a daily dose of 0.1 to 10 mg/kg, preferably 0.3 to 5 mg/kg and in particular 0.5 to 3 mg/kg of body weight, if appropriate in the form of several, preferably 1 to 3, individual administrations, to achieve the desired results. An individual administration contains the active compound or compounds in amounts of 0.1 to 5 mg/kg, preferably 0.2 to 3 mg/kg and in particular 0.4 to 2 mg/kg of body weight. For administration by inhalation, it is advantageous to administer the active compound or compounds in a daily dose of 0.1 to 10 mg, preferably 0.5 to 5 mg and in particular 1 to 3 mg, if appropriate in the form of several, preferably 1 to 3, individual doses.

Formulations for intravenous administration are expedient, in particular, for acute treatment, for example emergency treatment.

The therapeutic administration of the pharmaceutical formulation can take place 1 to 4 times daily at fixed or varying points in time, for example before each meal and/or in the evening. However, it may be necessary to deviate from the dosages mentioned, and in particular to do so as a function of the nature, body weight and age of the individual to be treated, the nature and severity of the disorder, the type of formulation and of administration of the medicament, and the period or interval within which administration takes place. Thus, in some cases it may be sufficient to manage with less than the abovementioned amount of active compound, whilst in other cases the abovementioned amount of active compound must be exceeded. In acute cases, a higher dose is administered at the start of the treatment. When the desired effect starts, the dose is reduced to a lower level. The optimum dosage and type of administration, of the active compounds, required in each particular case can be determined by any expert on the basis of his expert knowledge.

The pharmaceutical formulations as a rule consist of the active compounds according to the invention and non-toxic, pharmaceutically acceptable medicament excipients, which are used as an admixture or diluent in solid, semi-solid or liquid form, or as a means of encasing, for example in the form of a capsule, a tablet coating, a sachet or some other container for the therapeutically active constituent. An excipient can, for example, serve as a promoter of the absorption of the medicament by the body, as a formulating auxiliary, as a sweetener, as a flavor correctant, as a colorant or as a preservative.

Examples of forms which may be used orally are tablets, coated tablets, hard and soft capsules, for example made of gelatin, dispersible powders, granules, aqueous and oily suspensions, emulsions, solutions or sirups.

Tablets may contain inert diluents, for example calcium carbonate, calcium phosphate, sodium phosphate or lactose; granulating and dispersing agents, for example maize starch or alginates; binders, for example starch, gelatin or gum arabic; and lubricants, for example aluminum stearate or magnesium stearate, talc or silicone oil. The tablets may additionally be provided with a coating, which can also be such that delayed dissolution and absorption of the medicament in the gastrointestinal tract and hence, for example, better tolerance, a protracted effect or a retarded effect are achieved. Gelatin capsules can contain the medicament mixed with a solid diluent, for example calcium carbonate or kaolin, or an oily diluent, for example olive oil, groundnut oil or paraffin oil.

Aqueous suspensions, which, if appropriate, are prepared at short notice, may contain suspending agents, for example sodium carboxymethylcellulose, methylcellulose, hydroxypropylcellulose, sodium alginate, polyvinylpyrrolidone, gum tragacanth or gum arabic; dispersing agents and wetting agents, for example polyoxyethylene stearate, heptadecaethyleneoxycetanol, polyoxyethylenesorbitol monooleate, polyoxyethylene sorbitan monooleate or lecithin; preservatives, for example methyl or propyl hydroxybenzoates; flavoring agents; and sweeteners, for example sucrose, lactose, sodium cyclamate, dextrose or invert sugar syrup.

Oily suspensions may contain, for example, groundnut oil, olive oil, sesame oil, coconut oil or paraffin oil, and thickeners, such as, for example, beeswax, hard paraffin or cetyl alcohol; and furthermore sweeteners, flavoring agents and antioxidants.

Water-dispersible powders and granules may contain the medicaments mixed with dispersing agents, wetting agents and suspending agents, for example those mentioned above, as well as with sweeteners, flavoring agents and colorants.

Emulsions may contain, for example, olive oil, groundnut oil or paraffin oil, in addition to emulsifying agents, such as, for example, gum arabic, gum tragacanth, phosphatides, sorbitan monooleate or polyoxyethylene sorbitan monooleate, and sweeteners and flavoring agents.

For rectal administration of the medicaments, suppositories which are prepared with the aid of binders which melt at the rectal temperature, for example cacao butter or polyethylene glycol, are used.

For parenteral administration of the medicaments, sterile-injectable aqueous suspensions, isotonic salt solutions or other solutions, which, if appropriate, are to be prepared at short notice and which contain dispersing agents or wetting agents and/or pharmacologically acceptable diluents, for example propylene glycol or butylene glycol, are used.

Oral administration of the medicaments is preferred.

For use as a bronchospasmolytic agent, administration of the compounds according to the invention by inhalation is also preferred. These compounds are administered either directly as powders or by atomizing solutions or suspensions containing the compounds according to the invention. Atomizing can thereby be effected in the conventional manner, for example by compressed air atomizers or ultrasound atomizers. Administration from spray cans, especially those with a conventional metering valve (metered aerosols) is particularly advantageous. By means of metered aerosols, it is possible to provide a defined amount of active compound per spray jet. So-called synchronous inhalers with which administration of the active compound can be synchronized with inhalation are of particular advantage here. Suitable synchronous inhalation devices are disclosed, for example, in German Patent Specification 1,945,257, German Patent Specification 1,917,911 and German Offenlegungsschrift 2,055,734.

For inhalation purposes, the active compounds are preferably used in micronized form, particle sizes of less than 10 μm being advantageous. For administration from spray cans, the active compounds are dispersed in customary propellants, preferably with the aid of a dispersing agent. Possible propellants are, in particular, mixtures of trichlorofluoromethane (Frigen ® 11) and dichlorodifluoromethane (Frigen ® 12, it being possible for all or some of the trichlorofluoromethane to be replaced by 1,1,2-trichlorotrifluoroethane (Frigen ® 113). Possible dispersing agents are, in particular, the sorbitan esters customary for these purposes (Span ® from Atlas GmbH) and lecithin. The dispersing agent is dissolved in the propellant component of lower volatility, which has been initially introduced in cooled form. The micronized active compound is stirred or the micronized active compounds are stirred into the solution. The dispersion is filled into spray cans. After crimping, the more highly volatile propellant component is forced in.

The active compound or compounds can also be in micro-encapsulated form, if appropriate together with one or more of the excipients or additives mentioned.

Tablets containing 100 mg of
6-(4-isopropoxy-3-methoxyphenyl)-3[2H]pyridazinone 40 kg of active compound, 24 kg of lactose and 16 kg of maize starch are granulated with 4 kg of polyvinylpyrrolidone (molecular weight ~25,000) in 5.5 liters of water and the granules are forced through a sieve of 1.25 mm mesh width. After drying, 10 kg of carboxymethylcellulose, 4 kg of talc and 2 kg of magnesium stearate are added. The granules are compressed to tablets 9 mm in diameter, 250 mg in weight and with a hardness of 4 to 5 kg on a cam-type machine.

Capsules containing 15 mg of 6-(3-methoxy-4-n-propoxyphenyl)-3[2H]pyridazinone 150 mg of active compound, 845 mg of microcrystalline cellulose and 5 mg of amorphous silica are finely powdered, the powder is mixed thoroughly and size 4 hard gelatin capsules are filled with the mixture.

Metered aerosol formulation containing 6-(4-isobutoxy-3-methoxyphenyl)-3[2H]pyridazinone 0.540 g of Span° 85 and 0.135 g of aroma are dissolved in 10.215 g of cooled Frigen ® 11. 0.270 g of micronized active compound are stirred into the solution and 24 ml cans are filled with the mixture. After crimping, 14.971 g of Frigen ®12 are forced in. With a chamber volume of the metering valve of 125 μl, 1.6 mg of active compound are released as an aerosol per valve stroke.

Biological investigations

The 6-aryl-3[2H]pyridazinones of the general formula I have a bronchospasmolytic and/or cardiotonic action which in some cases is considerably superior to that of theophylline or theophylline-ethylenediamine. In addition, they have a more powerful bronchospasmolytic or positive inotropic action than 6-(4-methoxyphenyl)-3[2H]pyridazinone, as the comparison on known experimental designs shows.

The relaxing action of the 6-aryl-3[2H]pyridazinones I has been tested in vitro on a chain of tracheal rings (Tr.) of guinea pigs. The positive inotropic action was tested in vitro on the electrically stimulated left atrium of rats (l.a.). The quotient of $[EC_{40pot.}]_{left\ atrium}$ and $[ED_{50}]_{trachea}$ serves as a measure of the organ-selective activity. The quotients of the $[EC_{50}]_{trachea}$ values and $[ED_{40pot.}]_{left\ atrium}$ values for theophylline and the tested compound are reported as a measure of activity.

The compounds are identified in the Tables which follow by a serial number, as follows:

1: 6-(4-isopropoxy-3-methoxyphenyl)-3[2H]pyridazinone
2: 6-(3-methoxy-4-n-propoxyphenyl)-3[2H]pyridazinone
3: 6-(4-n-butoxy-3-methoxyphenyl)-3[2H]pyridazinone
4: 6-(4-ethoxy-3-methoxyphenyl)-3[2H]pyridazinone
5: 6-(4-allyloxy-3-methoxyphenyl)-3[2H]pyridazinone
6: 6-[3-methoxy-4-(3-methylbutoxy)-phenyl]-3[2H]pyridazinone
7: 6-(4-sec.-butoxy-3-methoxyphenyl)-3[2H]pyridazinone
8: 6-(3-ethoxy-4-methoxyphenyl)-3[2H]pyridazinone
9: 6-(3-allyloxy-4-methoxyphenyl)-3[2H]pyridazinone
10: 6-(4-methoxy-3-n-propoxyphenyl)-3[2H]pyridazinone
11: 6-(4-methoxy-3-isopropoxyphenyl)-3[2H]pyridazinone
12: 6-[4-methoxy-3-(3-methylbutoxy )-phenyl]-3[2H]pyridazinone
13: 6-(3-methoxy-4-n-propoxyphenyl)-3[2H]pyridazinethione
14: 6-(3-ethoxy-4-methoxyphenyl)-3[2H]pyridazinethione
15: 6-(4-methoxy-3-isobutoxyphenyl)-3[2H]pyridazinone
16: 6-(3-methoxy-4-isobutoxyphenyl)-3[2H]pyridazinone
17: 6-(4-methoxy-3-isopropoxyphenyl)-3[2H]pyridazinethione
18: 6-(3-isobutoxy-4-methoxyphenyl)-3[2H]pyridazinethione
19: 6-(4-methoxyphenyl)-3[2H]pyridazinone

TABLE 1

| Serial No. | Bronchospasmolytic and positive inotropic action, toxicity | | | | | |
|---|---|---|---|---|---|---|
| | A | B | C | D | E | F |
| 1 | 5.72 | 4.65 | 11.8 | 70.8 | 18.6 | 270 |
| 2 | 6.38 | 5.14 | 17.4 | 324 | 57.6 | 530 |
| 3 | 5.60 | 5.18 | 2.6 | 53.8 | 63.2 | >761* |
| 4 | 5.88 | 5.42 | 2.9 | 102 | 109 | |
| 5 | 5.82 | 5.18 | 4.4 | 85.2 | 63.1 | |
| 6 | 6.15 | 4.04 | 219 | 190 | 4.6 | >800* |
| 7 | 5.88 | 5.46 | 2.6 | 102 | 120 | |
| 8 | 6.47 | 5.88 | 3.9 | 398 | 316 | 550 |
| 9 | 6.27 | 5.90 | 2.3 | 251 | 331 | 610 |
| 10 | 6.33 | 6.20 | 1.3 | 288 | 661 | 770 |
| 11 | 7.01 | <3.0 | 10000 | 1370 | — | 600 |
| 12 | 6.30 | <3.0 | 2000 | 269 | — | 960 |
| 13 | 5.51 | <3.0 | 324 | 43.7 | — | |
| 14 | 5.85 | 5.68 | 1.5 | 95.5 | 200 | |
| 15 | 6.14 | 6.43 | 0.5 | 186 | 1122 | |
| 16 | 6.54 | 5.78 | 5.8 | 468 | 251 | |
| 17 | 5.14 | 5.56 | 0.4 | 18.6 | 151 | — |
| 18 | 5.39 | 5.80 | 0.6 | 33.1 | 166 | |
| 19 | 5.05 | 3.77 | 19.1 | 15.1 | 4.7 | >400* |
| Theophylline | 3.87 | 3.38 | 3.1 | 1 | 1 | 280 |

Column A: $-Lg[EC_{50}]_{trachea}$
Column B: $-Lg[EC_{40\ pot.}]_{Left\ atrium}$
Column C: $[EC_{40\ pot.}]/[EC_{50}]$
Column D: $[EC_{50theophylline}/[EC_{50}]_{substance}$
Column E: $[EC_{40\ pot.}]_{theophylline}/[EC_{40\ pot.}]_{substance}$
Column F: Approximate LD50, mouse p.o., values with * are data on the tolerated dose.

The bronchospasmolytic action of the compounds on the chain of tracheal rings of the guinea pig was tested in vitro:

Four parallel chains of tracheal rings, each consisting of 6 individual rings, of guinea pigs( ♂ and ♀, 430–600 g) in an organ bath [5 ml, Krebs-Henseleit solution with added phentolamine ($10^{-5}$ mol/l), 37° C., initial tension of the organs 2 g, gassing with carbogen] develop a stable, spontaneous tonic contraction after about 20 to 30 minutes. Relaxation of these permanently contracted organs can be caused, under isometric measurement conditions, by application of the test substance in cumulatively-semilogarithmically increasing concentration (for example $1\times10^{-6}+2\times10^{-6}+7+10^{-6}+2\times10^{-5}$ etc. mol/l), a constant relaxation response being waited for after each individual dose of the test substance before the next higher concentration is administered. Over a period of 20 to 30 minutes, a complete dose/action curve of the test substance is thus obtained. The particular relaxation is expressed as a percentage fraction of the maximum relaxation which can be achieved by administration of (−)isoprenaline ($10^{-6}$ mol/1). The concentration of the test substance which causes 50% of the maximum relaxation which can be achieved, expressed by the negative logarithm of the $EC_{50}$ mol/l: $-lg[EC_{50}]$ is a measure of the bronchodilator activity.

The positive inotropic action of the compounds was tested in vitro on the electrically stimulated left atrium of rats.

Isometric contractions (HSE force sensor K-30; Watanabe recorder, Linear Corder Mark 5) of isolated, left atria from rats ( ♂, 250–300 g) in an organ bath (10 ml, Tyrode nutrient solution, 31° C., gassing with carbogen, initial tension of the organs 0.25 g) under electrical stimulation (HSE stimulator, 7 V, 3 ms, 2 Hz) were recorded. After an equilibration time of 30 minutes, a dose-dependent increase in the contraction force can be caused by application of the test substance in cumulatively-semilogarithmically increasing concentration (for example $1\times10^{-6}+2\times10^{-6}+7\times10^{-6}+2\times10^{-5}$ etc. mol/l), a constant inotropic response being waited for after each individual dose of the test subtance before the next higher concentration is administered. The particular increase in the contraction force is expressed in % of the starting value before administration of the substance. The concentration of the test substance which potentiates the contraction force of the atrium by 40% compared with the starting value [$EC_{40pot}$.mol/l], expressed by the negative logarithm of the [$EC_{40pot}$.mol/l]: -lg[$EC_{40pot}$] serves as a measure of the cardiotonic activity.

The toxicity studies are carried out on female NMRI mice (body weight 23–30 g). The animals (5 animals per dose) receive food and water ad libitum. Various doses of the substances are administered once as a suspension in methocel via a gavage. The period of observation lasts 7 days. The tolerated dose (TD), that is to say the highest dose at which as yet none of the animals die, is determined by observation. The average lethal dose ($LD_{50}$), that is to say the dose at which 50% of the animals die, is determined from the dose/action curve by means of linear regression.

The in vitro findings are supported by the results of in vivo studies, as can be seen from measurements of bronchospasmolysis in guinea pigs and cardiac contractility in guinea pigs and cats.

Table II shows the results of testing of the inhibition of histamine-induced bronchospasm in anesthetized guinea pigs. Compounds 2, 11, 15 and 16 prove to be significantly more effective than theophylline.

TABLE II

Percentage inhibition of histamine-induced bronchospasm

| Minutes after administration | | 2 | 10 | 20 | 30 | 45 | 60 |
|---|---|---|---|---|---|---|---|
| Serial No. 2 | $Vmax_i$ | 126 | 17 | 9 | 5 | — | — |
| 5 μmol/kg i.v. | $Vmax_e$ | 104 | 16 | 12 | 7 | — | — |
| | $TV_i$ | 95 | 14 | 8 | 4 | — | — |
| Serial No. 2 | $Vmax_i$ | 143 | 76 | 57 | 37 | — | 17 |
| 20 μmol/kg i.v. | $Vmax_e$ | 118 | 66 | 54 | 44 | — | 23 |
| | $TV_i$ | 110 | 57 | 43 | 32 | — | 11 |
| Serial No. 2 | $Vmax_i$ | 3 | 47 | 21 | 35 | 40 | 56 |
| 5 μmol/kg i.j. | $Vmax_e$ | 6 | 48 | 30 | 38 | 52 | 60 |
| | $TV_i$ | 4 | 35 | 27 | 32 | 28 | 57 |
| Serial No. 11 | $Vmax_i$ | 152 | 113 | 89 | 47 | — | 9 |
| 20 μmol/kg i.v. | $Vmax_e$ | 123 | 109 | 63 | 43 | — | 6 |
| | $TV_i$ | 117 | 84 | 54 | 38 | — | 5 |
| Serial No. 15 | $Vmax_i$ | 172 | 119 | 110 | 82 | — | 60 |
| 20 μmol/kg i.v. | $Vmax_e$ | 108 | 123 | 103 | 84 | — | 46 |
| | $TV_i$ | 99 | 107 | 104 | 63 | — | 33 |
| Serial No. 16 | $Vmax_i$ | 154 | 73 | 48 | 34 | — | 15 |
| 20 μmol/kg i.v. | $Vmax_e$ | 145 | 63 | 60 | 33 | — | 16 |
| | $TV_i$ | 153 | 66 | 46 | 28 | — | 13 |
| Theophylline | $Vmax_i$ | 49 | 11 | 8 | 8 | — | — |
| 20 μmol/kg i.v. | $Vmax_e$ | 51 | 10 | 9 | 13 | — | — |
| | $TV_i$ | 45 | 5 | 5 | 10 | — | — |
| Theophylline | $Vmax_i$ | 95 | 38 | 19 | 18 | — | 7 |
| 60 μmol/kg i.v. | $Vmax_e$ | 79 | 27 | 15 | 15 | — | 8 |
| | $TV_i$ | 78 | 27 | 16 | 16 | — | 3 |
| Theophylline | $Vmax_i$ | 6 | 42 | 46 | 45 | 39 | 39 |
| 60 μmol/kg i.j. | $Vmax_e$ | 8 | 33 | 41 | 40 | 33 | 32 |
| | $TV_i$ | 7 | 35 | 41 | 37 | 33 | 37 |

$Vmax_i$ maximum flow rate of the respiratory air during inspiration
$Vmax_e$ maximum flow rate of the respiratory air during expiration
$BV_i$ breath volume A method for simultaneously recording pharmacodynamic and toxic effects on internal sensitive receptors, on the respiration and the cardiovascular system of guinea pigs was used [U. Kilian, E. Müller, E. Ch. Dittmann and J. Hamacher, Arzneimittel-Forschung 28 (II) 1699–1708, 1978]. The pneumotachogram of anesthetized (ethylurethane, 1.25 g/kg i.p.), monovagotomized, spontaneously breathing guinea pigs (♂, 350–450 g) was recorded. To characterize the bronchospasm induced by histamine (0.09–0.18 μmol /kg i.v.), the maximum flow rate of the respiratory air during inspiration ($Vmax_i$) and expiration ($Vmax_e$) and the breath volume ($BV_i$) were measured. A histamine spasm before administration of the substance was compared with several histamine spasms after administration of the substance. The test substances were administered intravenously (i.v.) and/or intrajejunally (i.j.). 5 to 10 animals were used per measurement, and the arithmetic mean was calculated from the results.

TABLE III

Protective effect against acetylcholine-induced bronchospasm in conscious guinea pigs

| Serial No. | Dose [μmol/kg]p.o. | Test 30 min. p.o. Doubling (tripling) of the latency period in N of 10 animals |
|---|---|---|
| 1 | 100 | 8 (8) |
| 2 | 60 (*) | 7 (5) (**) |
| 10 | 100 | 6 (6) |
| 10 | 300 | 10 (8) |
| 13 | 100 | 6 (6) |
| 15 | 100 | 10 (10) |
| 16 | 100 | 8 (5) |
| Theophylline | 100 | 6 (4) (***) |

(*) Administered in 4% strength methocel suspension
(**) Test 45 min. after administration: 5(5)
(***) Test 45 min. after administration: 3(2)

The figure in parentheses indicates the number out of 10 animals in which the latency period more than tripled.

The latency period is to be understood to be the time from the start of acetylcholine-atomization until clear signs of asthma appeared.

It is clear from Table III, that compounds 1, 2, 10, 13, 15 and 16 produce a greater protective effect against the bronchospasm in conscious guinea pigs caused by acetylcholine-atomization than does the comparison substance theophylline.

The test procedure was derived from that of T. Olsson, Acta Allergologica 26, 438–447(1971): guinea pigs (250–350 g) in a closed plexiglass cylinder (volume 5 l) are exposed to a mist of acetylcholine (0.06% in 0.9% sodium chloride solution; Heyer Use 77 ultrasonic atomizer) twice at an interval of 20 minutes. The time from the start of atomization to the onset of clear respiratory exertion (in certain circumstances, hypoxic convulsion in the lateral position) is measured, and is denoted the latency period.

In the control test (without administration of the substance), the latency period is 2 minutes. The test substance is administered orally by gavage (standard dose 100 μmol/kg, volume 1 ml of 4% strength methocel suspension in 0.9% strength sodium chloride solution/kg). After 30 minutes, the animals are again exposed to the acetylcholine mist, and the latency periods are measured. Prolongation of the latency period to at least twice its length is regarded as a protective effect.

Table IV below shows the results obtained on Langendorff guinea pig hearts with substances according to the invention compared with theophylline, amrinone and 6-(4-methoxyphenyl)-3[2H]pyridazinone (serial no. 19).

TABLE IV

Percentage increase in the left-ventricular pressure and the heart rate in guinea pig hearts isolated and perfused by the Langendorff method.

| Serial No. | Left-ventricular pressure | | Heart rate | |
|---|---|---|---|---|
| | EC$_{20}$[nMol] | E$_{max}$ after nMol | at EC$_{20}$ | at E$_{max}$ |
| 2 | 25 | 59 | 300 | 8 | 13 |
| 4 | 22 | 58 | 300 | 6 | 27 |
| 5 | 14 | 185 | 1000 | 3 | 9 |
| 7 | 13 | 86 | 1000 | 3 | 23 |
| 9 | 50 | 53 | 500 | 7 | 21 |
| 10 | 40 | 61 | 500 | 9 | 19 |
| 19 | 160 | 45 | 1000 | 6 | 11 |
| Theo-phylline | — (*) | 16 | 3000 | — | 5 |
| Amrinone | 1410 | 35 | 3000 | 7 | 8 |

(*) EC$_{20}$: is not reached
EC$_{20}$: dose which leads to a 20% increase in the left ventricular pressure
E$_{max}$: Maximum percentage increase in the left-ventricular pressure which can be reached with the indicated dose of the test substance The compounds according to the invention show a considerably greater increasing effect on the left-ventricular pressure than do the comparison substrates. In this context, it is particularly important that the increase in the heart rate is only inconsiderable.

The measurement of the left-ventricular pressure, the heart rate and the coronary flow was carried out on isolated and perfused hearts (Langendorff hearts) of guinea pigs (♂ and ♀, 400-500 g). After the animals have been sacrificed by a blow to the neck and exsanguination through the carotid arteries, the thoracic cavity is opened, and the aorta is exposed and looped up with a thread. A cannula, which is attached by tubing to the apparatus from which the nutrient solution slowly drops, is introduced in the direction of the heart and the heart is, quickly after removal from the thorax, connected to the perfusion apparatus. A balloon probe, connected to a Statham pressure sensor, is advanced through a cut through the left atrium into the left ventricle, and is provided with an initial pressure of 40 mm Hg. Coronary perfusion is carried out at constant pressure (60 cm H$_2$O) from a Mariott flask containing Krebs-Henseleit solution (37° C., gassing with carbogen). The nutrient solution flowing freely from the coronary sinus into the right atrium is measured with a flow meter (Grefe, Lüdenscheid) and, together with the change in the left-ventricular pressure and the heart rate determined from this, is recorded on a Watanabe recorder. The substances are administered in a volume of 0.1 ml of nutrient solution, in the dosage indicated in Tab. IV, within 2 sec., into the perfusion tubing close to the heart, successively in increasing doses to 5 hearts per substance and dose.

Table V below shows the results of measurement of the maximum rate of pressure rise in the right ventricle of guinea pigs.

TABLE V

Percentage change in the heart function dP/dt$_{max}$ of guinea pigs

| Serial No. | Dose [μmol/kg]i.v. | dP/dt$_{max}$ [Minutes] after administration | | |
|---|---|---|---|---|
| | | 0-10 (Maximum) | 10 | 30 |
| 2 | 0.3 | 36 | 5 | 2 |
| | 1 | 115 | 25 | 30 |
| | 3 | 168 | 68 | 47 |
| 4 | 0.3 | 39 | 12 | 23 |
| | 1 | 140 | 26 | 56 |
| | 3 | 95 | 66 | 59 |
| 10 | 0.3 | 42 | 16 | 21 |
| | 1 | 97 | 45 | 46 |
| | 3 | 164 | 90 | 66 |
| Amrinone | 0.3 | 33 | 8 | 13 |
| | 1 | 40 | 21 | 15 |
| | 3 | 66 | 13 | 20 |
| | 10 | 101 | 39 | 29 |
| | 30 | 141 | 78 | 69 |
| Theo-phylline | 10 | 59 | 12 | 20 |
| | 30 | 92 | 53 | 67 |
| | 100 | 147 | 135 | 112 | dP/dt$_{max}$: Maximum rate of pressure rise in the right ventricle.

It is clear from the values in Table V that the compounds according to the invention which were investigated have stronger positive inotropic effects (increase in dp/dt$_{max}$) than do the comparison substances amrinone and theophylline.

The effect of the substances on the contractility of the heart of guinea pigs is tested on animals (♂, 400 to 1000 g) under urethane anesthesia. The change in pressure in the right ventricle of the heart is measured with a tip catheter introduced through the right jugular vein and the maximum rate of pressure rise (dP/dt$_{max}$) is determined from this. The heart rate is derived from the pressure waves. No noticeable increases in the heart rate were found. The test substances were administered intravenously. 5-7 animals were used for each measurement, and the arithmetic mean was calculated from the results.

Table VI below shows the results of measurment of the percentage maximum rate of pressure rise in the left ventricles of cats. The comparison compounds investigted were amrinone and theophylline-ethylenediamine.

TABLE VI

Percentage change in the heart function dP/dt$_{max}$ in the cat

| Serial No. | Dose [μmol/kg]i.V. | dP/dt$_{max}$ | | | |
|---|---|---|---|---|---|
| | | 3 | 10 | 30 | 60 |
| | | (Minutes after administration) | | | |
| 2 | 0.3 | 55 | 31 | 26 | 37 |
| | 1 | 89 | 57 | 30 | 31 |
| 5 | 0.3 | 27 | 12 | 11 | 13 |
| | 1 | 64 | 25 | 15 | 20 |
| 7 | 0.3 | 36 | 4 | 1 | 2 |
| | 1 | 90 | 25 | 11 | 11 |
| Theophylline-ethylenediamine | 3 | 8 | 2 | 2 | 1 |
| | 10 | 62 | 30 | 22 | 26 |
| Amrinone | 1 | 17 | 6 | 7 | 23 |
| | 3 | 52 | 42 | 40 | 43 |
| | 10 | 70 | 67 | 59 | 55 | dP/dt$_{max}$: Maximum rate of pressure rise in the left ventricle.

The stated dose for theophylline-ethylenediamine relates to the content of theophylline.

Substances 2, 5 and 7 have stronger positive inotropic effects effects (increase in dP/dtmax) than do the comparison compounds, without leading to any considerable increase in the heart rate or end-diastolic ventricular pressure.

The effect of the substances on the contractility of the heart in cats was tested on animals (♂, ♀, 3.2 to 5.2 kg) under anesthesia with chloralose/urethane. The change in pressure in the left ventricle of the heart was measured with a tip catheter introduced through the right carotid artery, the R peak in the ECG (bipolar chest lead) initiating a signal to record the end-diastolic pressure; in addition, the maximum rate of pressure rise (dP/dtmax) was determined from the change in pressure. The heart rate was derived from the pressure waves. The test substances were administered intravenously. 2–6 animals were used per measurement, and the arithmetic mean was calculated from the results.

Measurements of blood pressure and heart rate after administration of compounds according to the invention to anesthetized rats showed no adverse findings.

We claim:

1. A 6-aryl-3[2H]pyridazinones of formula I

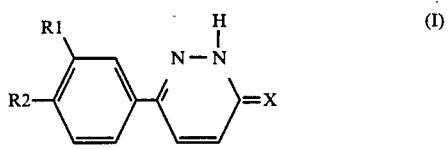

wherein one of the substituents R1 or R2 denotes a methoxy group and the other denotes an alkoxy group with 2 to 5 carbon atoms or an alkenyloxy group with 3 to 5 carbon atoms, and X denotes an oxygen atom or a sulfur atom, or a pharmacologically-acceptable salt thereof with a base.

2. A 6-aryl-3[2H]pyridazinone of claim 1 of formula Ia

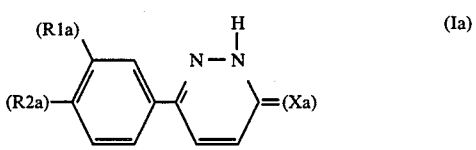

wherein
R1a denotes a methoxy group,
R2a denotes an alkoxy group with 2 to 4 carbon atoms or an alkenyloxy group with 3 or 4 carbon atoms and
Xa denotes an oxygen atom, or a pharmacologically-acceptable salt thereof with a base.

3. A 6-aryl-3[2H]pyridazinone of claim 1 of formula Ib

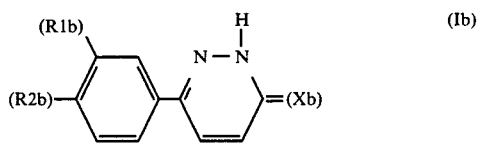

wherein
R1b denotes an alkoxy group with 2 to 4 carbon atoms or an alkenyloxy group with 3 or 4 carbon atoms,
R2b denotes a methoxy group and
Xb denotes an oxygen atom, or a pharmacologically-acceptable salt thereof with a base.

4. Compound according to claim 1, in which X denotes an oxygen atom.

5. The compound of claim 1, which is 6-(3-Methoxy-4-n-propoxyphenyl)-3[2H]pyridazinone.

6. The compound of claim 1 which is 6-(3-isobutoxy-4-methoxyphenyl)-2[2H]pyridazinone.

7. A brochospasmolytic medicament composition containing pharmaceutical excipient and an effective amount of one or more compounds according to claim 1.

8. A 6-aryl-3[2H]pyridazinone of claim 1 wherein X denotes a sulfur atom, or a pharmacologically-acceptable salt thereof.

9. A 5-aryl-3[2H]pyridazinone of claim 1 wherein one of R1 and R2 denotes an alkenyloxy group with from 3 to 5 carbon atoms, or a pharmacologically-acceptable salt thereof.

10. A 6-aryl-3[2H]pyridazinone of claim 9 wherein X denotes an oxygen atom, or a pharmacologically-acceptable salt thereof.

11. A 6-aryl-3[2H]pyridazinone of claim 9 wherein X denotes a sulfur atom, or a pharmacologically-acceptable salt thereof.

12. In prophylaxis of or treating disease based on a disorder of the bronchi, a process which comprises administering an effective amount of a compound according to claim 1 to a mammal in need of such therapy.

13. A process according to claim 12 wherein the compound is 6-(3-methoxy-4-n-propoxyphenyl)3[2H]pyridazinone.

* * * * *